United States Patent [19]

Nadelson et al.

[11] Patent Number: 5,378,728
[45] Date of Patent: Jan. 3, 1995

[54] BENZOIC ACID DERIVATIVES AS ANTIDIABETIC AGENTS

[75] Inventors: Jeffrey Nadelson, Denville; William R. J. Simpson, Mendham; Robert C. Anderson, Andover, all of N.J.; Joginder S. Bajwa, Stroudsberg, Pa.

[73] Assignee: Sandoz Ltd., Basel, Switzerland

[21] Appl. No.: 123,957

[22] Filed: Sep. 20, 1993

Related U.S. Application Data

[63] Continuation of Ser. No. 970,754, Nov. 3, 1992, abandoned.

[51] Int. Cl.⁶ .................. C07C 69/78; C07C 233/64
[52] U.S. Cl. ............................ 514/507; 514/544; 514/568; 514/621; 514/622; 560/51; 562/442; 562/459; 564/155; 564/158; 564/169
[58] Field of Search .............. 564/169, 155, 158; 562/442, 459; 560/51; 514/507, 544, 568, 621, 622

[56] References Cited

U.S. PATENT DOCUMENTS 4,623,662  11/1986  De Vries ........................ 514/596

FOREIGN PATENT DOCUMENTS 0900178  1/1985  Belgium.
0463989  1/1992  European Pat. Off..

OTHER PUBLICATIONS

De Vries et al., J. Med. Chem. (1986), vol. 29, pp. 1131–1133.
Chem. Abs., 109:93863r, Takahashi et al., 1988.
Brinkhaus et al., Tetrahedron (1986), vol. 42, pp. 553–560.

Primary Examiner—Johann Richter
Assistant Examiner—Michael B. Hydorn
Attorney, Agent, or Firm—Robert S. Honor; Melvyn M. Kassenoff; Thomas O. McGovern

[57] ABSTRACT

Compound of the formula

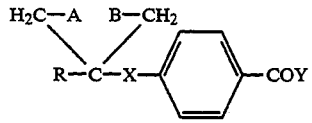

where R is $CH_3(CH_2)_m$,
A and B are hydrogen, a bond or $-(CH_2)_n$,
X is

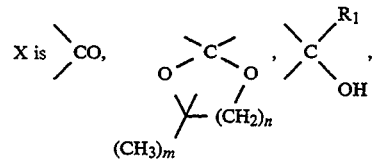

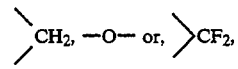

m is 0, 1, 2 or 3, n is 1, 2, or 3,
$R_1$ is hydrogen or lower alkyl, and
Y is $-OH$, $-OR_2$ or $-NR_3R_4$
where $R_2$, $R_3$ and $R_4$ are hydrogen or unsubstituted or substituted alkyl, aryl and aralkyl substituents.

28 Claims, No Drawings

BENZOIC ACID DERIVATIVES AS ANTIDIABETIC AGENTS

This is a continuation application of Ser. No. 07/970,754, filed Nov. 3, 1992, now abandoned.

This invention relates to tertiary alkyl and cycloalkyl substituted benzoic acid derivatives and their use as antidiabetic agents. More particularly, this invention concerns para substituted ketones, ketals, alcohols, ethers and alkyl derivatives of benzoic acid, benzoic acid esters and benzoic acid amides and imides. This invention also relates to pharmaceutical compositions containing these compounds as the active ingredient.

The compounds of this invention may be represented by the following structural formula:

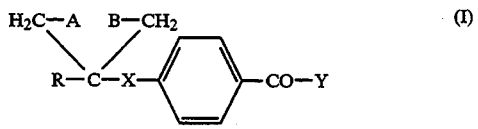
(I)

where R is $CH_3(CH_2)_m-$,

A and B are each hydrogen or together are a bond or $-(CH_2)_n-$,

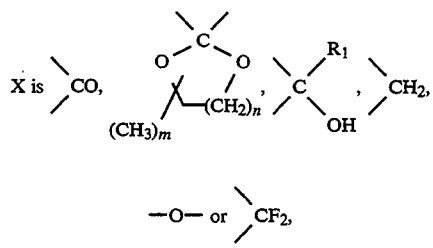

$-O-$ or $\diagdown C F_2$, m is 0, 1, 2 or 3 and n is 1, 2 or 3, $R_1$ is hydrogen or lower alkyl, that is, alkyl of 1 to 4 carbon atoms, for example, methyl, ethyl, isopropyl and the like, and a) Y is $-OH$ or $-OR_2$, where $R_2$ is lower alkyl, phenyl, phenalkyl of 7 to 9 carbon atoms, $-(CH_2)_n-CONR_3R_4$, $-(CH_2)_nOCOR_3$,

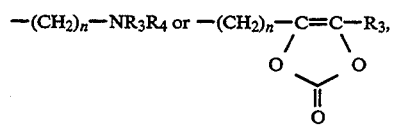

$R_3$ and $R_4$ are independently hydrogen or lower alkyl, with the proviso that when X is $>CO$ and A and B are each hydrogen, Y is other than $-OH$ or $OR_2$, where $R_2$ is lower alkyl; or b) Y is $-NR_5R_6$
where
i) $R_5$ is hydrogen or lower alkyl and
$R_6$ is hydrogen, lower alkyl, $-OR_3$, $-(CH_2)_n-SH$ or $-CHR_7-COOR_3$ and
$R_7$ is hydrogen, lower alkyl, or

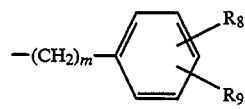

where $R_8$ and $R_9$ are each independently hydrogen, hydroxy, halogen, that is, fluorine, chlorine, bromine or iodine, lower alkyl, or lower alkoxy, that is, alkoxy having 1 to 4 carbon atoms, for example, methoxy ethoxy, isopropoxy, and the like, and m, n and $R_3$ are as defined above, or ii) $R_5$ is hydrogen, lower alkyl, $-COR_{10}$ or

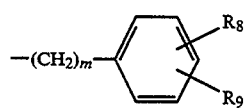

where $R_{10}$ is lower alkyl or $-OR_3$, and m, $R_3$, $R_7$ and $R_8$ are as defined above, and $R_6$ is

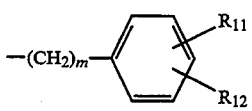

where $R_{11}$ and $R_{12}$ are each independently hydrogen, halogen, lower alkyl, lower alkoxy, $-CF_3$, $-(CH_2)_mCOOR_3$, $-CONR_3R_4$, $-SO_3H$, or $-PO_3H_2$ and m, $R_3$ and $R_4$ are as defined above, or iii) $R_5$ is hydrogen, lower alkyl, $OR_3$

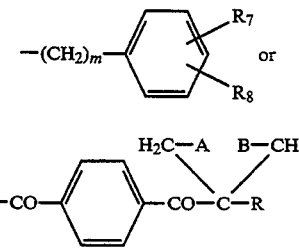

where m, A, B, R, $R_3$, $R_7$ and $R_8$ are as defined above and
$R_6$ is $-COR_{13}$
where $R_{13}$ is alkyl of 1 to 8 carbon atoms, phenalkenyl of 8 to 10 carbon atoms,

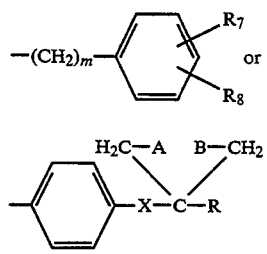

where m, A, B, R, $R_7$ and $R_8$ are as defined above, and pharmaceutically acceptable salts of compounds having a free acid group or pharmaceutically acceptable acid additions salts of compounds having a basic nitrogen group.

Preferred compounds of formula (I) are those in which in substituent X is >CO or a ketal in which m is O and n is 1 or 2, expecially 1. More preferably, A and B are hydrogen, X is >CO and Y is —NR$_5$R$_6$. Expecially preferred are the compounds of groups ii and iii, in particular, the compounds of group iii, in which R$_5$ is hydrogen or methyl.

The compounds of formula (I) in which Y is the ester group —OR$_2$ may be prepared in accordance with the following reaction scheme:

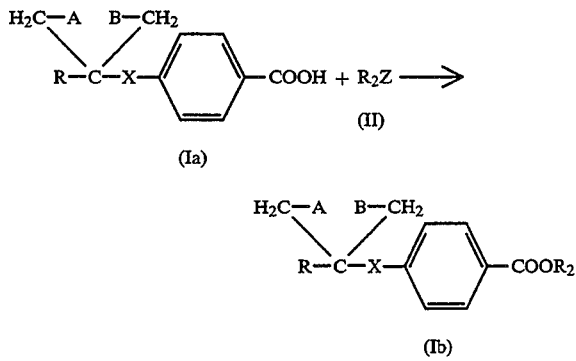

where Z is chlorine, bromine or iodine and R, A, B, X and R$_2$ are as defined above.

The compounds of formula (Ib) are prepared by esterifying a compound of formula (Ia) with a compound of formula (II) in the presence of an alkali metal base, preferably lithium, potassium or sodium carbonate. Although a solvent is not critical, it is preferred that the reaction be carried out in an inert solvent such as ketones, e.g., acetone; ethers such as diethyl ether and tetrahydrofuran; aliphatic or aromatic hydrocarbons, e.g., hexane or benzene; or an excess of compounds (Ia) and/or (II), in particular acetone. The temperature at which the reaction is carried out is not critical, but 20° C. to reflux temperature, especially reflux temperature is preferred. The reaction time is also not critical, but it is preferred that the reaction be run for 5 to 25 hours, in particular 8 to 18 hours. The compound of formula (Ib) is isolated by conventional techniques, e.g., distillation or recrystallization.

The compound of formula (I), in which Y is an amide of group i or group ii, where R$_5$ is other than —COR$_{10}$ may be prepared in accordance with the following reaction scheme:

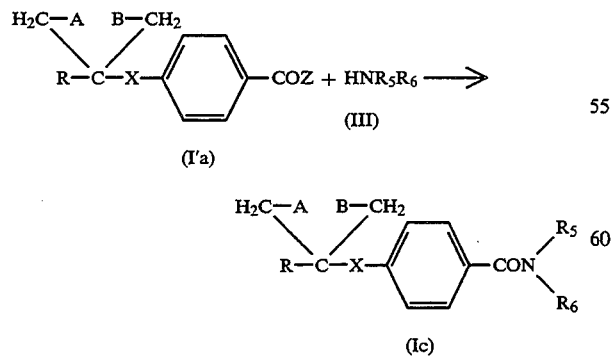

where R, A, B, X, Z, R$_5$ and R$_6$ are as defined above in group i or in group ii provided R$_5$ in group ii is other than —COR$_{10}$.

The compounds of formula (Ic) are prepared by reacting a compound of the formula (Ia) with a compound of formula (III). Although a solvent is not required, it is preferred that the reaction be carried out in an inert solvent, for example ethers, such as diethyl ether or tetrahydrofuran, aliphatic hydrocarbons, such as hexane, aromatic hydrocarbons, such as benzene, and halogenated hydrocarbons, such as methylene chloride, especially tetrahydrofuran. An acid scavenging agent, such as triethylamine, diethylisopropylamine, pyridine or an alkali metal carbonate, such as potassium carbonate, can also be present in the reaction mixture. The temperature at which the reaction is carried out is not critical, but it is preferred that the reaction be run between about −78° to ±80° C., preferably −10° C. to 50° C., and more preferably between about 0° C. to 25° C. The time of the reaction also is not critical, but it is preferred that the reaction be carried out for about 30 minutes to about 24 hours, preferably 30 minutes to about 5 hours, especially 1 to 3 hours. In carrying out this procedure with the N-phenyl benzamides the acid chloride (I'a) is preferably added dropwise to the amine (III) at a temperature of from about −78° to 10° C., preferably −50° to −30° C. over a period of about 30 minutes to 3 hours, preferably 1 to 2 hours; and after addition, the reaction mixture is stirred at 0 ° to +80° C., preferably room temperature, for 3 to 24 hours preferably 16 to 20 hours. The compound of formula (Ic) is isolated by conventional techniques, e.g., evaporation and recrystallization.

The compound of formula (Ic) wherein the substituent R$_6$ contains a carboxylic substituent may also be prepared by hydrolyzing an ester form, in particular a lower alkyl ester form, using standard procedures. For example, the ester may be dissolved in a suitable solvent or co-solvents such as a lower alkanol or tetrahydrofuran or mixtures thereof, at a temperature of from 20° to 55° C., preferably 30° to 40° C., following which an aqueous sodium or potassium hydroxide solution is added dropwise over a period of 30 minutes to 3 hours, preferably about 2 hours. After. addition, the solution is stirred for about 3 hours to about 24 hours, preferably about 16 to 20 hours. The carboxylic acid substituted product is isolated by acidification, for example, with hydrochloric acid, followed by filtration. The compound of formula (I) in which Y is an imide of group ii where R$_5$ is —COR10 or of group iii may be prepared in accordance with the following reaction scheme:

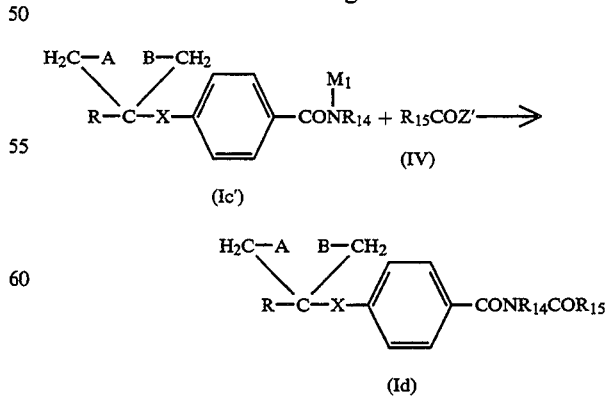

where M$_1$ is lithium, sodium, or potassium, and either
  R$_{14}$ is the same as R$_6$ in group if,
  R$_{15}$ is the same as R$_{10}$ in group ii, and Z′ is —OCOCH₃, when R₁₅ is lower alkyl, or the same as Z, when R₁₅ is —OR₃ or R₁₄ is M or the same as R₅ as defined in group iii, R₁₅ is the same as R₁₃ as defined in group iii and Z′ is the same as Z, and R, A, B, X and R10 are as define above.

The compounds of formula (Id) are prepared by reacting a compound of formula (Ic') with a compound of the formula IV in an inert water free solvent. The amide salt (lc') is preferably formed in situ by reacting the amide corresponding to (Ic') with an alkali metal hydride or amide prior to reacting with the acid chloride (IV). It is also preferred that about 3 equivalents of alkali metal hydride or amide per equivalent of amide (Ic') be used in the reaction. It has also been found that for the iraides of group iii, the yield is substantially improved if the acid chloride IV is added very slowly over about a two hour period to the amide salt Ic'. Although the particular solvent used is not critical, it is preferred that the reaction be carried out in an inert solvent such as dimethyl formamide (DMF), ethers, e.g., diethyl ether or tetrahydrofuran, aliphatic hydrocarbons, such as hexane, or aromatic hydrocarbons, such as benzene or toluene, especially tetrahydrofuran. The temperature at which the reaction is carried out is not critical, but it is preferred that the reaction be run between about −10° to 75° C., for example, about −10° C. to 50° C., preferably between about 0° C. to 20° C. The time of the reaction also is not critical and can run up to 100 hours, but it is preferred that the reaction be carried out for about 30 minutes to 24 hours and more preferably about 30 minutes to 5 hours, especially 1 to 3 hours. The compound of formula (Id) is isolated by conventional techniques, e.g., chromatography and crystallization.

The compound of formula (I) in which X is an acetal and Y is —OH may be prepared in accordance with the following reaction scheme:

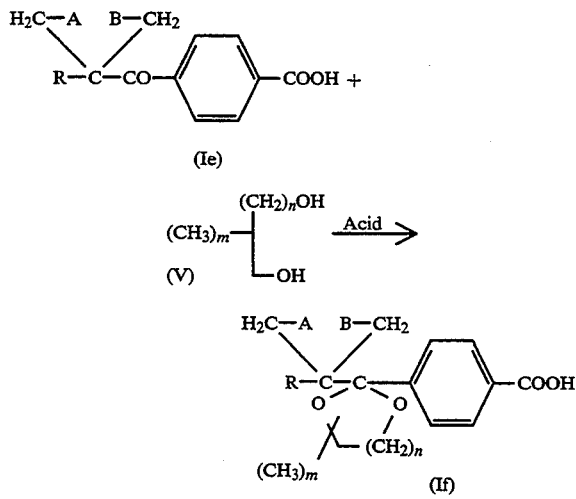

where R, A, B, m and n are as defined above.

The compound of formula (If) are prepared by reacting a compound of formula (ie) with a compound of formula (V) in the presence of an acid catalyst. The catalyst can be a sulfonic acid such as toluene sulfonic acid or a mineral acid, e.g., hydrochloric acid or sulfuric acid, preferably, toluene sulfonic acid. Although a solvent is not required., it is preferred that the reaction be carried out in an inert solvent such as the aliphatic or aromatic hydrocarbons, mentioned above, allcyclic hydrocarbons, such as cyclohexane or in excess glycol (V), especially toluene and excess glycol. The temperature at which the reaction is run is not critical; but 500° C. to reflux temperature is preferred, especially reflux temperature. The time of the reaction is also not critical, but it is preferred that the reaction be carried out for 10 to 48 hours, especially 16 to 30 hours. The compound of formula (If) is isolated by adding a base, e.g., sodium or potassium hydroxide, and water; reacting to form an aqueous solution; separating the aqueous layer from the organic layer and acidifying to precipitate the free acid. The final product is separated by filtration and purified by conventional techniques, e.g., washing and drying.

The compound of formula (I) in which X is >CHOH may be prepared in accordance with the following reaction scheme:

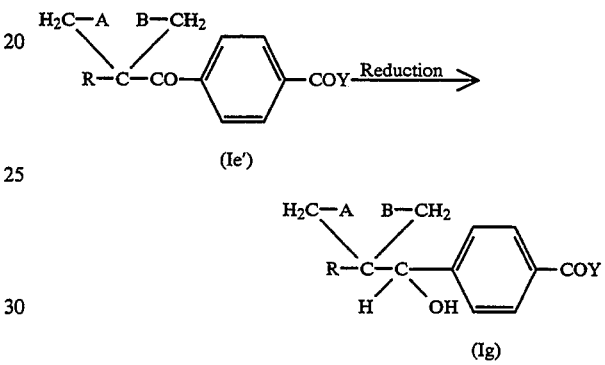

where R, A, B and Y are as defined above.

The compounds or formula (Ig) are prepared by reducing a compound of formula (Ié) with a carbonyl reducing agent. The reducing agents include lithium aluminum hydride, 3.5 molar sodium bis (2-methoxyethoxy) aluminum hydride in toluene (Red-A1), or sodium borohydride. When Y is —OH, lithium aluminum hydride is preferred; and when Y is —OR₂ or —NR5R₆, sodium borohydride is preferred. Although a solvent is not required, it is preferred that the reaction be carried out in an inert solvent such as the ethers for example, tetrahydrofuran, the aliphatic, aromatic or cycloaliphatic hydrocarbons indicated above, lower alkanols, for example, ethanol, and methylene chloride or mixtures thereof, especially tetrahydrofuran. The temperature at which the reaction is carried out is not critical, but it is preferred that the reaction be run between about −40° C. to 30° C., preferably between about −40° C. to 10° C. The time of the reaction also is not critical, but it is preferred that the reaction be carried out for 30 minutes to 5 hours, especially 1 to 3 hours. The compound of formula (Ig) is isolated by conventional techniques, e.g., extraction and evaporation.

The compound of formula (I) in which X is >CR₁OH, may be prepared in accordance with the following reaction scheme:

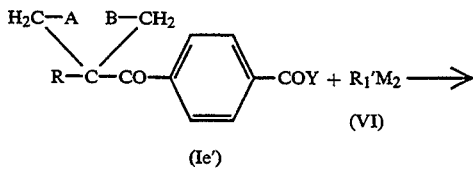

-continued

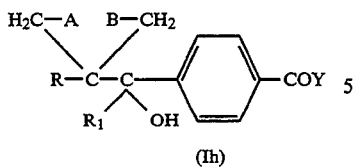

(Ih)

where $R_1$, is lower alkyl,

R, A, B and Y, are as defined above and $M_2$ is lithium or magnesium halide.

The compounds of formula (Ih) are prepared by reacting a compound of the formula (Ié) with a compound of the formula (VI) in an inert solvent. Although the solvent is not critical, it is preferred that the reaction be carried out in the ethers or aliphatic, aromatic or cycloaliphatic hydrocarbons mentioned above, especially diethyl ether or tetrahydrofuran. The temperature at which the reaction is run is not critical, but it is preferred that the reaction be carried out between about 200° C. to the reflux temperature of the solvent, preferably at the reflux temperature. The time of the reaction also is not critical, but it is preferred that the reaction be carried out for 2 to 10 hours, especially 4 to 7 hours. The compound of formula (Ih) is isolated by conventional techniques, e.g., extraction with an aqueous base and acidification to precipitate the acid.

The compound of formula (I) in which X is >CO: >$CF_2$ or >$CH_2$ may be prepared in accordance with the following reaction scheme:

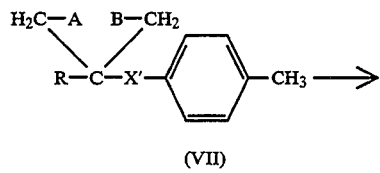

(VII)

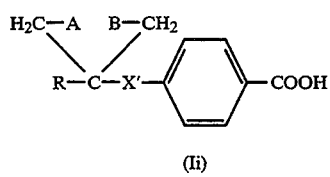

(Ii)

where R, A, and B are as defined above and X' is >CO, >$CF_2$ or >$CH_2$.

The compounds of formula ( I i ) are prepared by oxidizing a compound of formula (VII) with a strong oxidizing agent in an aqueous amine solvent in the presence of an alkali metal base such as sodium hydroxide or potassium hydroxide. The amine used as solvent is a tertiary amine such as pyridine or triethylamine preferably pyridine. The temperature at which the reaction is carried out is not critical but it is preferred that the reaction be run between about 70° C. and the reflux temperature of the reaction mixture, preferably the reflux temperature. The time of the reaction also is not critical, but it is preferred that the reaction be carried out for 1 to 10 hours, especially 3 to 7 hours. The compound of formula (Ii) is isolated by conventional techniques, e.g., evaporation and recrystalization.

The compound of formula (I) in which X is —O— may be prepared in accordance with the following reaction scheme:

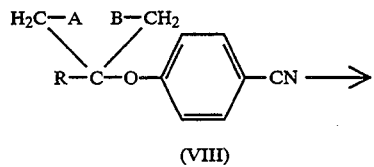

(VIII)

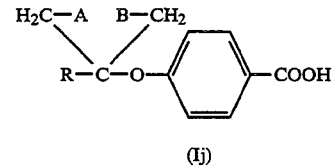

(Ij)

where R, A, and B are as defined above.

The compounds of formula (Ij) are prepared by hydrolyzing a compound of the formula (VIII) with an alkali metal base in a lower alkanol and acidifying the resulting salt. The alkaline metal base can be sodium hydroxide or potassium hydroxide; and the lower alkanol can be methanol, ethanol, isopropanol, butanol and the like, preferably ethanol. The temperature at which the reaction is carried out is not critical, but it is preferred that the reaction be run between about 300° C. and the reflux temperature of the reaction mixture, preferably the reflux temperature. The time of the reaction also is not critical, but it is preferred that the reaction be carried out for 3 to 16 hours, especially 12 to 24 hours. The compound of formula (Ij) is isolated by conventional techniques, e.g., acidification, extraction and chromatography.

The compound of formula VII in which X is >$CF_2$ may be prepared in accordance with the following reaction scheme:

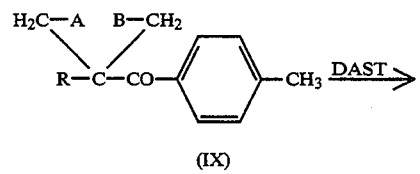

(IX)

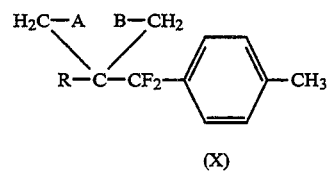

(X)

where R, A and B are as defined above and DAST is diethylaminosulfurtrifluoride.

The compounds of formula (X) are prepared by fluorinating a compound of the formula (IX) with DAST. Although a solvent is not required, it is preferred that the reaction be carried out in excess DAST with an inert co-solvent such as benzene, hexane and the like. The temperature at which the reaction is carried out is not critical, but it is preferred that the reaction be run between about 0° C. to 100° C., preferably between about 30° C. to 60° C. The time of the reaction also is not critical, but it is preferred that the reaction be carried out for 6 to 36 hours, especially 12 to 24 hours. It is preferred that the reaction be carried out in an inert atmosphere such as argon, helium, or nitrogen, preferably nitrogen. The compound of formula (X) is isolated by conventional techniques, e.g., extraction, evaporation and chromatography.

The compound of formula (VIII) may be prepared in accordance with the following reaction scheme:

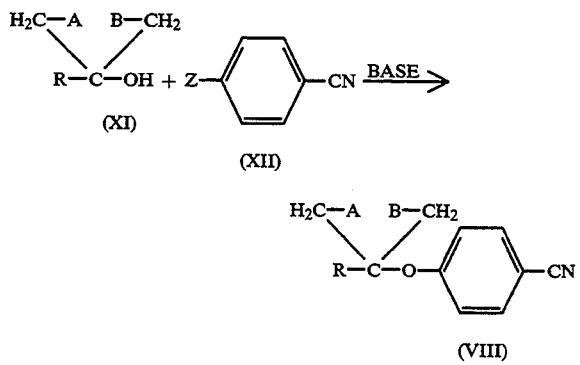

R, A, B, and Z are as defined above.

The compounds of formula (VIII) are prepared by reacting a compound of the formula (XI) with a compound of the formula (XII) in an inert solvent in the presence of a strong base. The strong base can be sodium hydride, potassium hydride, sodium or potassium amide and the like. Although the particular solvent used is not critical, it is preferred that the reaction be carried out in an inert solvent such as dimethylsulfoxide, dimethyl formamide, benzene, hexane and the like, especially dimethylsulfoxide (DMSO). The temperature at which the reaction is carried out is not critical, but it is preferred that the reaction be run between about 0° C. to 100° C., preferably between about 30° C. to 60° C. The time of the reaction also is not critical, but it is preferred that the reaction be carried out for 6 to 36 hours, especially 12 to 24 hours. It is also preferred that the reaction be carried out in an inert atmosphere such as argon, helium, or nitrogen, preferably nitrogen. The compound of formula (VIII) is isolated by conventional techniques, e.g., evaporation.

Many of the compounds of formula II, III, V, VI, VII, VIII, IX, X, XI and XII are known and may be prepared by methods described in the literature. Similarly, many of the compounds of formula (IV) in which $R_{15}$ is the same as $R_{10}$, defined in group ii, or in which $R_{15}$ is alkyl, phenalkenyl, substituted or unsubstituted phenyl or phenalkyl as defined in group iii are also known and may be prepared by methods disclosed in the literature. The known compounds not specifically described may be prepared by analogous method or as described in the examples below using known starting materials. The compounds of formula Ia and Ib in which R is lower alkyl, A and B are hydrogen and X is >CO and their use as anti-diabetic agents are disclosed in U.S. Pat. No. 4,015,010. The compound of formula Ii in which R is methyl, A and B are hydrogen and X' is methylene is also known.

The compounds of formula I in which $R_2$ is —$(CH_2)_nNR_3R_4$ may be administered in free base form or in pharmaceutically acceptable acid addition salt form. Such salts may be prepared in conventional manner and exhibit the same order of activity as the free bases. The compounds of formula I in which Y is OH or in which $R_2$ or $R_6$ in group i or $R_6$ in groups ii contains a free carboxylic, sulphonic or phosphonic acid group may be administered in acid form or in salt form with a pharmaceutically acceptable cation. Such salts may be prepared in conventional manner and also exhibit the same order of activity as the free acids.

Certain compounds of formula (I), such as the compounds where X is >$CR_1OH$ or $R_6$ is —CH-$R_7$—$COOR_3$ and $R_7$ is other than hydrogen, may exist in the form of optically active isomers and can be separated and recovered by conventional techniques. Similarly, compounds of the invention containing a double bond can exist in the form of geometric isomers, which can also be readily separated and recovered by conventional procedures. Such isomeric forms are included in the scope of this invention.

As indicated above, the compounds of formula (I) exhibit pharmacological activity in animals. In particular, the compounds of formula (I) are antidiabetic agents and are useful in the treatment of diabetes, as indicated by acute chronic hypoglycemic screening in male Sprague-Dawley rats, given 1 to 100 mg/kg of drug orally. The rats, 2 to 3 months of age, weighing 250 to 280 grams, are kept in a room at a controlled ambient temperature of 72° F. and a 12/12 hour light (6:00 AM to 6:00 PM)/dark cycle. Purina chow and water are available ad libitum; and at fed state, 37.5 mg of streptozotocin/kg body weight are injected via the tail vein. One week later, those rats are considered to be diabetic with fed blood glucose of 180 to 260 ml/dl; overnight fasting level less than 80 ml/dl; and 3 hour post oral glucose tolerance blood glucose of 41 to 80 mg/dl. Blood glucose is determined with a YSI Glucose Analyzer. The chronic screen tests are carried out as follows:

On Day 1, food is removed from rats at 9:00 A.M.; and after an initial blood glucose reading is taken via the tail vein, vehicle (control) or compound (9 rats/treatment) is administered orally. Six hours later blood glucose level is measured; and immediately thereafter the rats are refed. The same rats are given either vehicle or drug once a day for two consecutive days. Blood glucose is then determined after a 6-hour fast post dosing on Day 3. The ED 50 value is the amount of compound required to produce a 50% reduction on Day 3 of the average increase in blood glucose level induced by streptozotocin.

The antidiabetic effective dosage of the compounds of formula (I) employed for the alleviation of diabetes will vary depending on the particular compound employed, the mode of administration and severity of the condition being treated. However, in general, satisfactory results are obtained when the compounds of formula (I) are administered at a daily dosage of from about 1 milligram to about 100 milligrams per kilogram of animal body weight, optionally given in divided doses two to four times a day, or in sustained release form. For the larger mammals, the total daily dosage is from about 5 to about 500 milligrams per day. Unit dosage forms comprise from about 1 to about 500 milligrams of the active compound in intimate admixture with a solid or liquid pharmaceutically acceptable carrier or diluent. The compounds of the invention may be administered in similar manner to known standards for use as antidiabetes agents. The suitable daily dosage for a particular compound will depend on a number of factors, such as its relative potency of activity. It has been determined that the preferred compound of the invention 4-(2,2-dimethyl-1-oxopropyl)-N-[4-(2,2-dimethyl-1-oxopropyl) benzoyl]-benzamide, has an ED50 of 30 mg/kg/day in the chronic test. An indicated daily dose for the compound is from about 100 to about 500, preferably 250 to 500 mg p.o. for the larger primates such as humans.

For the above use, the compounds of formula (I) may be administered orally or parenterally as such or admixed with conventional pharmaceutical carriers. They may be administered orally in such forms as tablets, dispersible powders, granules, capsules, syrups and elixirs, and parenterally as solutions or emulsions. The compositions for oral use may contain one or more conventional adjuvants, such as sweetening agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., magnesium stearate, steric acid and talc. The tablets may be coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

Tablets and capsules containing the ingredients indicated below may be prepared by conventional techniques and are useful in treating diabetes at a dose of one or two tablets or capsules two to four times a day.

| Ingredient | Tablet | Weight (mg.) Capsule | Soft Gelatin Capsule |
|---|---|---|---|
| 4-(2,2-dimethyl-1-oxopropyl)-benzamide | 250 | 250 | 250 |
| polyvinylpyrrolidone | 15 | — | — |
| lactose | 332.5 | 396 | — |
| corn starch | 25 | — | — |
| talcum | 15 | — | — |
| colloidal silicon dioxide | 50 | 50 | — |
| magnesium stearate | 2.5 | — | — |
| stearic acid | — | 4 | — |
| soybean oil | — | — | 450 |
| | 700 mg. | 700 mg. | 700 mg. |

Similar tablets and capsules for treating diabetes can be prepared using 4-(2,2-dimethyl-1-oxopropyl)-N-[4-(2,2-dimethyl-1-oxopropyl)benzoyl]-benzamide or the remaining compounds of examples 1 to 17 disclosed below.

EXAMPLE I 4- (2,2-dimethyl-1-oxopropyl)-benzoic acid, (2-diethylamino-2-oxo) ethyl ester To 1.24 grams (6 mmoles) of 4-pivaloyl benzoic acid in 50 milliliters of acetone is added 1.68 grams (12 m moles) of potassium carbonate. The reaction mixture is refluxed for one hour and then 1.07 grams (7.2 mmoles) of 2-diethylamino-2-oxoethyl chloride is added. After refluxing overnight, the reaction mixture is cooled to room temperature. The salts are filtered off and washed with acetone, after which the combined filtrates are evaporated under vacuum. The crude product is recrystallized from hexane to yield 4-(2,2-dimethyl-1-oxopropyl)-benzoic acid, 2-(diethylamino-2-oxo)ethyl ester (71°–72° C.).

When the above reaction is carried out using an equivalent amount of:
a) 2-diethylaminoethyl chloride
b) 2,2-dimethyl-1-oxopropoxymethyl chloride or
c) (5-methyl-2-oxo-1,3-dioxol-4-yl) methyl chloride
in place of the 2-diethylamino-2-oxoethyl chloride, there is obtained:
a) 4-(2,2-dimethyl-1-oxopropyl)-benzoic acid, (2-diethylamino)ethyl ester (oil)
b) 4-(2,2-dimethyl- 1-oxopropyl)-benzoic acid, (2,2-dimethyl-1-oxopropoxy)methyl ester (m.p. 58°–60° C.) or
c) 4-(2,2-dimethyl-1-oxopropyl)-benzoic acid, (5-methyl-2-oxo-1,3-dioxol-4-yl)methyl ester, respectively.

Following the above procedure and using an equivalent amount of 2-(1,1-dimethylethyl)-2-(4-carboxyphenyl)-1,3-dioxolane from example 3 in place of the 4-pivaloyl benzoic acid, there is obtained 2-[4-[2-(diethylamino-2-oxo)ethoxy]carbonyl]phenyl]-2-(1,1-dimethylethyl)-1,3-dioxolane (m.p. 86° C.).

When this reaction is carried out using 2-(1,1-dimethylethyl)-2-(4 carboxyphenyl)-1,3-dioxolane and in the place of the 2-diethylamino-2-oxoethyl chloride, an equivalent amount of
d) ethyl chloride
e) (2,2-dimethyl-1-oxopropoxy)methyl chloride
f) 2-(diethylamino)ethyl chloride or
g) (5-methyl-2-oxo-1,3-dioxol-4-yl)methyl chloride, there is obtained
d) 2-(1,1-dimethylethyl)-2-(4-ethoxycarbonylphenyl)-1,3-dioxolane (m.p. 43°–45° C.)
e) 2-(1,1-dimethylethyl)-2- [[4-[2,2-dimethyl-1-oxopropoxy)methoxy]carbonyl]phenyl]-1,3-dioxolane (m.p. 104°–106° C.)
f) 2-[4-[2-(diethylamino)ethoxycarbonyl]phenyl]-2-(1,1-dimethylethyl)-1,3-dioxolane (b.p. 125° C/O.35 mm) or
g) 2-(1,1-dimethylethyl)-2-[4-([5-methyl-2-oxo-1,3-dioxol-4-yl)methoxycarbonyl]phenyl]1,3-dioxolane (m.p. 159°–161° C.), respectively

EXAMPLE 2

4-(1-methylcyclopropylcarbonyl)-benzoic acid, 4-(2,2-dimethyl-1-oxopropyl)-benzamide and 4-(2,2-dimethyl-1-oxopropyl)-N-[-4-(2,2-dimethyl-1-oxopropyl)-benzoyl]benzamide A) 4-(1-methylcyclopropyl carbonyl)-benzoic acid 6.0 grams (34.4 mmol) of 1-methylcyclopropyl-p-toluene ketone is dissolved in 150 milliliters of pyridine and 17.5 milliliter (35 mmol) of 2N sodium hydroxide and 150 milliliters of water are added. The reaction mixture is heated to 90° C. and 16.3 grams (103 mmol) of potassium permanganate are added in small portions over a ½ hour period. Heating is continued at 90° C. for an additional 2 hours, following which the reaction mixture is allowed to cool to room temperature. 30 milliliters of methanol are added, and the manganese dioxide is removed by vacuum filtration. The manganese dioxide residue is washed twice with 50 milliliters of methanol and twice with 50 milliliters of water. The combined filtrates are concentrated by vacuum and then redissolved in 200 milliliters of water. The solution is acidified with 2N hydrochloric acid, and the white crystalline precipitate formed is filtered off and washed twice with 50 milliliters of water. The crystalline residue is dried in vacuo to yield 4-(1-methylcyclopropylcarbonyl)-benzoic acid (m.p. 136°–137° C.).

When the above reaction is carried out using in place of the 1-methycyclopropyl-p-toluene ketone an equivalent amount of 1,1-dimethylpropyl-p-toluene ketone there is obtained 4-(2,2-dimethyl-1-oxobutyl)-benzoic acid (m.p. 128°–129° C.)

B) 4-(2,2-dimethyl-1-oxopropyl)-benzoyl chloride 12 grams (58 mmol) of 4-(2,2-dimethyl-1-oxopropyl)-benzoic acid in 30 milliliters of thionyl chloride are refluxed under nitrogen for 1½ hours. The excess thionyl chloride is then stripped off under reduced pressure to yield the crystalline acid chloride (m.p. 38°–39° C.).

Following the above procedure and using in place of the 4-(2,2-dimethyl-1-oxopropyl)benzoic acid an equivalent amount of a) 4-(2,2-dimethyl-1-oxobutyl)-benzoic acid or
4-(1-methylcyclopropyl carbonyl)-benzoic acid there is obtained a) 4-(2,2-dimethyl-1-oxobutyl)-benzoyl chloride or
b) 4-(1-methylcyclopropyl carbonyl)-benzoyl chloride respectively.

C) 4-(2,2-dimethyl-1-oxopropyl)-benzamide 3.1 grams (14 mmoles) of 4-(2,2-dimethyl-1-oxopropyl) benzoyl chloride is dissolved in 15 milliliters of diethylether, and the resulting solution is added dropwise to concentrated ammonium hydroxide with vigorous stirring at 0°–10° C. The white crystalline precipitate which forms is filtered off and washed with water and with ether. The product is dried in vacuo to yield 4-(2,2-dimethyl-1-oxopropyl)-benzamide (m.p. 138°–140° C.).

Following essentially the above procedure, but using in place of the concentrated ammonium hydroxide an equivalent amount of a) dimethylamine
b) methylamine
c) 4-fluoroaniline
d) aniline
e) t-butylamine
f) hydroxylamine
g) 4-aminobenzoic acid
h) 4-aminobenzoic acid, ethyl ester
i) 2-mercaptoethylamine
j) benzylamine
k) N-methylaniline or
l) phenethylamine there is obtained a) 4-(2,2-dimethyl-1-oxopropyl)-N,N-dimethylbenzamide (m.p. 87°–89° C.)
b) 4-(2,2-dimethyl-1-oxopropyl)-N-methylbenzamide (m.p. 128°–129° C.)
c) 4-(2,2-dimethyl-1-oxopropyl)-N-(4-fluorophenyl)benzamide (m.p. 145° C.)
d) 4-(2,2-dimethyl-1-oxopropyl)-N-phenylbenzamide (m.p. 132° C.)
e) 4-(2,2-dimethyl-1-oxopropyl)-N-(1,1-dimethylethyl) benzamide (m.p. 119° C.)
f) 4-(2,2-dimethyl-1-oxopropyl)-N-hydroxybenzamide (m.p. 126°–127° C.)
g) 4-(2,2-dimethyl-1-oxopropyl)-N-(4-carboxyphenyl) benzamide (m.p. 282°–284° C.)
h) 4-(2,2-dimethyl-1-oxopropyl)-N-(4-ethoxycarbonyl phenyl)benzamide (m.p. 159°–161° C.)
i) 4-(2,2-dimethyl-1-oxopropyl)-N-(2-mercaptoethyl) benzamide (m.p. 75°–76° C.)
j) 4-(2,2-dimethyl-1-oxopropyl)-N-benzylbenzamide (m.p. 150°–150.5° C.)
k) 4-(2,2-dimethyl-1-oxopropyl)-N-methyl-N-phenylbenzamide (m.p. 148°–148.5° C.) or
l) 4-(2,2-dimethyl-1-oxopropyl)-N-phenethylbenzamide (m.p. 118.5°–119° C.), respectively.

When a equivalent amount of
m) 4-(1-methylcyclopropylcarbonyl)benzoyl chloride or
n) 4-(2,2-dimethyl-1-oxobutyl)benzoyl chloride is used in place of the above 4-(2,2-dimethyl-1-oxopropyl)benzoyl chloride, there is obtained
m) 4-(1-methylcyclopropylcarbonyl)benzamide or
n) 4-(2,2-dimethyl-1-oxobutyl)benzamide (m.p. 121°–122° C.) respectively.

When the procedures of steps B and C above are carried out using an equivalent amount of 2-(1,1-dimethylethyl)-2-(4-carboxyphenyl)-1,3-dioxolane from example 3 in place of the 4-(2,2-dimethyl-1-oxopropyl)-benzoic acid, there is obtained 2-[4-carbamoyl)phenyl]-2-(1,1-dimethylethyl)-1,3-dioxolane (m.p. 182°–182.5° C.).

Following this procedure and using in place of the ammonia of step C, an equivalent amount of
o) dimethylamine
p) aniline
q) hydroxylamine
r) 2-mercaptoethylamine
s) glycine or
t) glycine, methyl ester, there is obtained
o) 2-[(4-dimethylaminocarbonyl)phenyl]-2-(1,1-dimethylethyl)-1,3-dioxolane (m.p. 140°–142° C.)
p) 2-(1,1-dimethylethyl)-2-[(4-phenylaminocarbonyl) phenyl]-1,3-dioxolane (m.p. 133° C.)
q) 2-(1,1-dimethylethyl)-2-[4-(hydroxyaminocarbonyl) phenyl]1,3-dioxolane (m.p. 163.5°–164.5° C.)
r) 2-(1,1-dimethyethyl)-2-[4-[(2-mercaptoethyl)amino carbonyl]phenyl]-1,3-dioxolane (m.p. 173°–175° C.),
s) 4-(2-[1,1 -dimethylethyl]-1,3-dioxolan-2-yl)benzoyl glycinamide (m.p. 202°–204° C.) or
t) 4-(2-[1,1-dimethylethyl]-1,3-dioxolan-2-yl)benzoyl glycinamide, methyl ester (m.p. 126°–127° C.), respectively.

D) 4-(2,2-dimethyl-1-oxopropyl)-N-[4-(2,2-dimethyl-1-oxopropyl)-benzoyl]benzamide 4.2 grams (20.5 mmoles) of 4-(2,2-dimethyl-1-oxopropyl) benzamide is dissolved in 100 milliliters of dry tetrahydrofuran. The solution is cooled to 0° C., and 3.7 grams (22.6 mmoles) of potassium hydride (from a 24.5% mixture in mineral oil) which has been washed free of oil with hexane, is added. After hydrogen evolution has ceased, (approximately 2 hours), a solution of 4.6 grams (20.5 mmoles) of 4-(2,2-dimethyl-1-oxopropyl)-benzoyl chloride in 20 milliliters of dry tetrahydrofuran is added dropwise at 0° C. When addition is complete, the reaction mixture is concentrated in vacuo, and the residue is then dissolved in methylene dichloride and filtered to remove solids. The filtrate is purified by flash chromatography (3 inch column and 0.3% then 1% methanol/methylene chloride to elute) and crystallized from diethyl ether to yield the title product (m.p. 131°–132° C.).

When an equivalent amount of 4-(2,2-dimethyl-1-oxopropyl)-N-methylbenzamide is used in place of the 4-(2,2-dimethyl-1-oxopropyl)benzamide above, there is obtained 4-(2,2-dimethyl-1-oxopropyl)-N-[4-(2,2- dimethyl-1-oxopropyl)benzoyl]N-methylbenzamide (m.p. 121.5°–122.5° C.).

When the above reaction is carried out, and an equivalent amount of benzoyl chloride or p-fluorobenzoyl chloride is used in place of the 4-(2,2-dimethyl-1-oxopropyl)benzoyl chloride, there is obtained 4-(2,2-dimethyl-1-oxopropyl)-N-benzoyl-benzamide (m.p. 121°–123° C.) or 4-(2,2-dimethyl-1-oxopropyl)-N-(p-fluorobenzoyl)-benzamide (m.p. 100°–101° C.) respectively.

EXAMPLE 3

2-(1,1-dimethylethyl)-2-(4-carboxyphenyl)-1,3-dioxolane

A mixture of 63.5 grams (0.31 mole) of 4-(2,2-dimethyl-1-oxopropyl)benzoic acid, 156 ml. of ethylene glycol, and 1 gram of toluenesulfonic acid in 600 ml of toluene is refluxed for 24 hours using a Dean-Stark trap to remove water. The mixture is then cooled and partially evaporated; and to the residue, 4.5 grams of solid potassium hydroxide are carefully added followed by 225 ml of water. The resulting mixture is refluxed for 1½ hours, cooled, filtered and the layers separated. The aqueous layer is acidified with 2N hydrochloric acid, and the resulting precipitate is removed by filtration. The precipitate is washed with water, then water/ethanol (5/1), and then petroleum ether. The product is dried in vacuo to yield the title product (m.p. 213.5°–215.5° C.).

When the above reaction is carried out and using in place of the 4-(2,2-dimethyl-1-oxopropyl)benzoic acid, an equivalent amount of a) 4-(1-methylcyclopropylcarbonyl) benzoic acid or b) 4-(2,2-dimethyl-1-oxobutyl) benzoic acid there is obtained a) 2-(4-carboxyphenyl)-2-(1-methylcyclopropyl)-1,3-dioxolane (m.p. 157°–159° C.) or b) 2-(4-carboxyphenyl)-2-(1,1-dimethylpropyl)-1,3-dioxolane (m.p. 194°–196° C.)

When the procedures of steps B and C of example 2 are carried out using in place of the 4-(2,2-dimethyl-1-oxopropyl)-benzoic acid an equivalent amount of a) 2-(4-carboxylphenyl)-2-(1-methylcyclopropyl)-1,3-dioxolane or b) 2-(4-carboxyphenyl)-2-(1,1-dimethylpropyl)-1,3-dioxolane, there is obtained c) 2-[(4carbamoyl)phenyl]-2-(1-methylcyclopropyl)-1,3-dioxolane (m.p. 144°–145° C.) or d) 2-[(4-carbamoyl)phenyl]-2-(1,1-dimethylpropyl)-1,3-dioxolane (m.p. 162°–163.5° C.).

EXAMPLE 4

4-carboxy-α-(1,1-dimethylethyl)benzenemethanol

To a mixture of 1.95 grams (0.051 mole) of lithium aluminum hydride and 30 ml. of tetrahydrofuran is added a solution of 10.5 grams (0.051 mole) of 4-(2,2dimethyl-1-oxopropyl)-benzoic acid in 110 ml. of tetrahydrofuran. The mixture is stirred for 2 hours at 0°–5° C., and then quenched by the addition of sodium sulfate solution. The resulting mixture is made acidic by the cautious add ition of concentrated hydrochloric acid. The mixture is extracted with ether; and the extracts are then washed with 50% brine, dried over magnesium sulfate, filtered and evaporated. The resulting solid is dissolved in aqueous sodium hydroxide, filtered and after acidification with hydrochloric acid, again extracted with ether, dried over magnesium sulfate, filtered and evaporated to yield the title product (m.p. 161.5°–163° C.).

When the above process is carried out using in place of the 4-(2,2-dimethyl-1-oxopropyl)benzoic acid an equivalent amount of a) 4-(2,2-dimethyl-1-oxobutyl)benzoic acid there is obtained a) 4-carboxy-α-(1,1-dimethylpropyl)-benzenemethanol (m.p. 142°–143° C.).

Following the above process and using in place of the lithium aluminum hydride and 4-(2,2-dimethyl-1-oxopropyl) benzoic acid, an equivalent amount of sodium borohydride and b) 4-(2,2-dimethyl-1-oxopropyl)benzoic acid, (2-diethylamino-2-oxo)ethyl ester c) 4-(2,2-dimethyl-1-oxobutyl)benzamide or d) 4-(2,2-dimethyl-1-oxopropyl)-N-(2-mercaptoethyl) benzamide, there is obtained b) 4-[(2-diethylamino-2-oxoethoxy)carbonyl]-α-(1,1-dimethylethyl)-benzenemethanol (m.p. 140°–141° C.)

c) 4-carbamoyl-α-(1,1-dimethylpropyl)-benzenemethanol (m.p. 207°–208° C.) or d) α-(1,1-dimethylethyl)-4-[(2-mercaptoethyl)aminocarbonyl]-benzenemethanol (m.p. 95.5°–101° C.) respectively.

EXAMPLE 5

4-carboxy-α-(1,1-dimethylethyl)-α-methyl)-benzenemethanol

To a solution of 12.36 grams (0.06 mole) of 4-(2,2-dimethyl-1-oxopropyl)benzoic acid in 250 ml. of tetrahydrofuran is added rapidly without cooling 100 ml(0.14 mole) of 1.4 M methyl lithium in ether. The temperature is allowed to rise to 45° C. and a heavy precipitate forms. The mixture is refluxed for 6 hours, then cooled, and the resulting mixture is treated with aqueous sodium hydroxide. The layers are separated, and the organic layer is washed with aqueous sodium hydroxide. The basic layers are combined and acidified with 2N hydrochloric acid. The resulting mixture is filtered, and the residue is recrystallized from ethyl acetate to yield the title product (m.p. 170°–172° C.).

EXAMPLE 6

4-(1,1-difluoro-2,2-dimethylpropyl)benzoic acid

A) 4-(1,1-difluoro-2,2-dimethylpropyl)toluene

A solution of 20.5 grams (116 mmoles) of p-pivaloyl toluene in 20.6 grams (128 mmoles) of DAST is warmed under nitrogen to 50° C. and stirred for 40 hours. The brown solution obtained is cooled to 0° C., and 150 ml. of 2M sodium bicarbonate is carefully added. This solution is extracted with 400 ml. of ethyl acetate and the extracts washed with 100 ml of brine. The ethyl acetate solution is then dried over magnesium sulfate, concentrated in vacuo to yield an orange oil, which is flash chromatographed on 500 grams of silica gel and eluted with hexane to give the title product as a colorless oil (Rf ketone 0.60; Rf difluoride 0.71; 95:5 heptane:ethyl acetate).

B) 4-(1,1-difluoro-2,2-dimethylpropyl)benzoic acid

A mixture of 13.5 grams (68.1 mmoles) of 4-(1,1-difluoro-2,2-dimethylpropyl) toluene, 6.8 grams (170 mmoles) of sodium hydroxide and 21.5 grams (136 mmoles) of potassium permanganate in 250 ml. of 1:1 pyridine:water is heated to 95° C. and stirred for 4 hours. This suspension is filtered, and the residue is wash with 300 ml. of water and 400 ml. of ethyl acetate.

The filtrate is concentrated in vacuo and then redissolved in 300 ml. of water. The aqueous solution is washed with 500 ml. of ethyl acetate and then acidified to pH2 with concentrated hydrochloric acid. This is extracted 3 times with 300 ml. of ethyl acetate, and the combined extracts are dried over magnesium sulfate and concentrated in vacuo to yield 4-(1,1-difluoro-2,2-dimethyl propyl)benzoic acid as a fine white powder. A portion of this material is recrystallized from diethyl ether to give colorless crystals of the acid (m.p. 196°–198° C.).

When steps B and C of example 2 are carried out using an equivalent amount of 4-(1,1-difluoro-2,2-dimethyl propyl)benzoic acid in place of the 4-(2,2-dimethyl-1-oxopropyl)benzoic acid, there is obtained 4-(1,1-difluoro-2,2-dimethylpropyl)benzamide (m.p. 128°–132° C.).

EXAMPLE 7

4-(1,1-dimethylethoxy)benzoic acid

A suspension of hexane washed sodium hydride (1.3 grams of a 60% suspension in oil) in 15 ml. of dry dimethylsulfoxide is heated at 70° C. under nitrogen for 1 hour. It is then cooled to 30° C. and 1.5 grams of tertiary butanol is slowly added. The resultant mixture is stirred for 30 minutes; and then 2.4 grams of para-fluorobenzonitrile is added and stirring is continued at room temperature-overnight. The reaction mixture is heated at 60° C. for 6 hours and then cooled and diluted with diethyl ether. The ether solution is washed with water and brine and is then dried over sodium sulfate and evaporated to give an oily residue. 3.3 grams of the residue is refluxed overnight with 5.0 ml. of 2N sodium hydroxide in 40 ml. of ethanol. The mixture is then concentrated to dryness, redissolved in water and washed with diethyl ether. The aqueous phase is acidired with 2N hydrochloric acid and then extracted with methylene chloride. The organic fractions are combined, dried over sodium sulfate and then evaporated to give an oil, which is Chromatographed on silica gel with methylene chloride as the eluant to yield the title compound as a crystalline product (m.p. 132°–133° C.)

The sodium salt is prepared by dissolving 194 mg. of the above acid in 1.0 ml. of 1.0N sodium hydroxide. The resultant solution is evaporated to dryness, triturated with ethanol and filtered to give the sodium salt.

When steps B and C of example 2 are carried out using an equivalent amount of 4-(1,1-dimethylethoxy) benzoic acid in place of 4-(2,2-dimethyl-1-oxopropyl)-benzoic acid there is obtained 4-(1,1-dimethylethoxy) benzamide (m.p. 135°–136° C.).

EXAMPLE 8

4-(2,2-dimethylpropyl)benzamide

When steps B and C of example 2 is carried out using an equivalent amount of 4-(2,2-dimethylpropyl)benzoic acid in place of the 4-(2,2-dimethyl-1-oxopropyl)benzoic acid, there is obtained 4-(2,2-dimethylpropyl)benzamide (m.p. 176°–177° C.).

EXAMPLE 9

4(2,2-dimethyl-1-oxopropyl)benzoyl-(L)-phenylaninamide 3.3 grams of L-phenylalanine are dissolved 10 milliliters of 2N sodium hydroxide and 10 milliliters of acetone. The solution is cooled to 0° to 10° C., and a solution of 1.68 grams of p-pivaloyl benzoyl chloride in 5 milliliters of acetone are added dropwise while maintaining the pH at 11 with the 2N sodium hydroxide. After 2 hours, the reaction mixture is allowed to warm to room temperature, following which it is acidified with 2N hydrochloric acid. The acetone is evaporated off and the residue is distributed between methylene chloride and water. The methylene chloride layer is separated from the water layer and dried with magnesium sulfate. The methylene chloride is evaporated off, and the residue is recrystallized from ether/hexane to yield white crystalline 4-(2,2-dimethyl-1-oxopropyl)-benzoyl-(L)-phenylalaninamide; m.p. 120°–123° C.; $[\alpha]_D^{25}$ 55.6(methanol).

When the above reaction is carried out using in place of the L-phenylalanine, an equivalent amount of
a) (D)-phenylalanine,
b) glycine, or
c) glycine, methyl ester there is obtained
a) 4-(2,2-dimethyl-1-oxopropyl)benzoyl-(D)-phenylalaninamide (m.p. 119°–121° C.; $[\alpha]_D^{25}$ +54°,methanol);
b) 4-(2,2-dimethyl-1-oxopropyl)benzoyl-glycinamide (m.p. 135°–136° C.); or
c) 4-(2,2-dimethyl-1-oxopropyl)benzoyl-glycinamide, methyl ester, respectively.

EXAMPLE 10

4-(2,2-dimethyl-1-oxopropyl)-N-methoxybenzamide

A solution of 67.2 grams of 4-(2,2-dimethyl-1-oxopropyl)-benzoyl chloride dissovled in 100 millimeters of tetrahydrofuran (THF) is added dropwise to a suspension of 25.0 grams of methoxyamine hydrochloride and 256 grams of finely ground anhydrous potassium carbonate in 1.1 liters of THF. The reaction mixture is stirred at 23° C. overnight and then heated to 50° to 55° C. for 5 hours. This mixture is cooled to room temperature and filtered. The residue is washed with THF, and the filtrates are combined and evaporated to dryness. The crude product is partitioned between 200 ml of chloroform and 200 ml of cold 1 molar sodium carbonate solution, following which the organic phase is separated from the aqueous phase, dried with magnesium sulfate and evaporated to dryness. The residue is recrystallized twice from methylene chloride/t-butyl methyl ether to yield the pure title compound (mp 126°–127.5° C.).

EXAMPLE 11

4-(2,2-dimethyl-1-oxopropyl)-N-(4-carboxyphenyl)-benzamide

A. 4-(2,2-dimethyl-1-oxopropyl)-N-(4-ethoxycarbonylphenyl) benzamide

A mixture of 247.5 grams (1.5 moles) of p-aminoethylbenzoate and 171.7 grams (1.7 moles) of triethylamine in 6 liters of ether is cooled to −30°; and 336 grams (1.5 moles) p-pivaloyl benzoyl chloride in 1.5 liters of ether is added dropwise while maintaining the temperature during addition between −30° and −50° C. At the end of the addition, the reaction mixture is allowed to warm to room temperature and is stirred overnight. One liter of water is then added to the mixture, and the stirring is continued for 2 hours at room temperature. The mixture is filtered and the solid obtained is washed with water and cold ether to yield the title product (M.P 157°–159° C.).

When the above teacitoh is carried out using in place of the p-aminoethylbenzoate an equivalent amount of:
a) m-aminoethylbenzoate;
b) o-aminoethylbenzoate;
c) p-toluidine;
d) p-trifluoromethylaniline;
e) p-aminophenacetic acid;
f) p-aminobenzenesulfonic acid;
g) p-aminobenzenephosphonic acid;
h) p-aminobenzamide;
i) 3-methoxy-4-aminoethylbenzoate;
j) 3-chloro-4-aminoethylbenzoate;
k) 2-bromo-4-aminoethylbenzoate;
l) 3-trifluormethyl-4-aminomethylbenzoate;
m) N-methyl-p-aminoethylbenzoate; or
n) N-benzyl-p-aminoethylbenzoate; there is obtained:
a) 4-(2,2-dimethyl-1-oxopropyl)-N-(3-ethoxycarbonylphenyl)-benzamide (m.p. 76.5°–77° C.);
4-(2,2-dimethyl-1-oxopropyl)-N-(2-methoxycarbonylphenyl)-benzamide (m.p. 109°–110° C.);
c) 4-(2,2-dimethyl-1-oxopropyl)-N-(4-tolyl)-benzamide (m.p. 144°–145° C.)
d) 4-(2,2-dimethyl-1-oxopropyl)-N-(4-trifluoromethylphenyl)-benzamide (m.p. 142°–143 ° C.);
e) 4-(2,2-dimethyl-1-oxopropyl)-N-(4-carboxy methylphenyl)-benzamide (m.p. 162°–163° C.)
f) 4-(2,2-dimethyl-1-oxopropyl)-N-(4-sulfophenyl)-benzamide;
g) 4-(2,2-dimethyl-1-oxopropyl)-N-(4-phosphonophenylbenzamide (m.p. 248°–250° C.);
h) 4-(2,2-dimethyl-1-oxopropyl)-N-(4-carbamoylphenylbenzamide;
i) 4-(2,2-dimethyl-1-oxopropy)-N-(2-methoxy-4-methoxy-carbonylphenyl)-benzamide (m.p. 134.5°–135.5° C.);
j) 4-(2,2-dimethyl-1-oxopropyl)-N-(2-chloro-4-ethoxycarbonylphenyl)-benzamide (m.p. 105.5°–106.5° C.);
k) 4-(2,2-dimethyl-1-oxopropyl)-N-(3-bromo-4-methoxycarbonylphenyl)-benzamide (m.p. 177°–180° C.);
l) 4-(2,2-dimethyl-1-oxopropyl)-N-(2-trifluoromethyl-4-methoxycarbonylphenyl)-benzamide (m.p. 125°–126° C.);
m) 4-(2,2-dimethyl-1-oxopropyl)-N-methyl-N-(4-methoxycarbonylphenyl)-benzamide (m.p. (122°–123° C.) or
n) 4-(2,2-dimethyl-1-oxopropy)-N-benzyl-N-(4-ethoxycarbonylphenyl)-benzamide (m.p. 88°–91° C.), respectively.

B. 4-(2,2-dimethyl-1-oxopropyl)-N-(4 carboxyphenyl)-benzamide

To a mixture of 2 liters of ethanol and 500 ml of methylene chloride is added in portions with heating 176.5 grams (0.5 moles) of the title compound of step A. When the addition is complete, the heat is removed; and 500 ml (0.5 mole) of 1N sodium hydroxide and 500 ml of water are added dropwise. The resulting solution is stirred overnight at room temperature. A portion of the solvent is evaporated off, and the residue is treated with water. The water phase is extracted with ether, following which 500 ml of 2N hydrochloric acid is added dropwise to the basic aqueous layer. The mixture is stirred at room temperature overnight and filtered. The product is washed with ethanol/water (1/9), then with water and finally with cold ether to yeild the title product (m.p. 282°–284° C.).

Following the above procedure, but using in place of the title compound of step A, an equivalent amount of:
a) 4-(2,2-dimethyl-1-oxopropyl)-N-(3-ethoxycarbonylphenyl)-benzamide;
b) 4-(2,2-dimethyl-1-oxopropyl)-N-(2-ethoxycarbonylphenyl)-benzamide;
i) 4-(2,2-dimethyl-1-oxopropyl)-N-(2-methoxy-4-ethoxycarbonylphenyl)-benzamide;
j) 4-(2,2-dimethyl-1-oxopropyl)-N-(2-chloro-4-ethoxycarbonylphenyl)-benzamide;
k) 4-(2,2-dimethyl-1-oxopropyl)-N-(3-bromo-4-ethoxycarbonylphenyl)-benzamide;
m) 4-(2,2-dimethyl-1-oxopropyl)-N-methyl-N-(4-ethoxycarbonyl-phenyl)-benzamide; or
n) 4-(2,2-dimethyl-1-oxopropyl)-N-benzyl-N-(4-ethoxycarbonyl-phenyl)-benzamide, there is obtained:
a) 4-(2,2-dimethyl-1-oxopropyl)-N-(3-carboxyphenyl)-benzamide (m.p. 229°–230° C.);
b) 2,2-dimethyl-1-oxopropyl)-N-(2-carboxyphenyl)-benzamide (m.p. 168°–169° C.);
i) 4-(2,2-dimethyl-1-oxopropyl)-N-(2-methoxy-4-carboxyphenyl)-benzamide (m.p. 208°–209° C.);
j) 4-(2,2-dimethyl-1-oxopropyl)-N-(2-chloro-4-carboxyphenyl)-benzamide (m.p. 281°–284° C.);
k) 4-(2,2-dimethyl-1-oxopropyl)-N-(2-bromo-2-carboxyphenyl)-benzamide (m.p. 260°–263° C.);
m) 4-(2,2-dimethyl-1-oxopropyl)-N-methyl-N-(4-carboxyphenyl)-benzamide (m.p. 208°–211° C.); or
n) 4-(2,2-dimethyl-1-oxopropyl)-N-benzyl-N-(4-carboxyphenyl)-benzamide (m.p. 196°–199° C.); respectively.

EXAMPLE 12

4-(2,2-dimethyl-1-oxopropyl)-N-ethoxycarbonyl-N-(4-ethoxycarbonylphenyl)-benzamide A solution of 5.3 grams of (0.015 m) of the title compound of example 11A in 25 ml of DMF is added to a suspension of 0.396 grams (0.0165 m) of sodium hydride in 25 ml of DMF. The mixture is stirred at room temperature lot 1 hours, and a solution of 1.63 g (0.015 m) of ethyl chloroformate in 5 ml DMF is added. The mixture is stirred overnight at room temperature, following which the reaction is quenched by the dropwise addition of water and ether. The insoluble material is filtered and washed with ether: petroleum either (1:2), and the resulting product is recrystallized from hexane to give the title compound (m.p. 84°–86° C.).

Following the above procedure but using an equivalent amount of acetic acid anhydride in place of the ethyl chloroformate, there is obtained 4-(2,2-dimethyl-1-oxopropyl)-N-acetyl-N-(4-ethoxycarbonylphenyl)-benzamide (m.p. 91°–94° C.).

EXAMPLE 13

4-(2,2-dimethyl-1-oxopropyl)-N-(3-phenylpropionyl)-benzamide

A slurry of potassium hydride (from 46 grams of 35% potassium hydride in oil washed three times with hexane)in 50 ml of THF is added with stirring under nitrogen to 20 grams of 3-phenylpropionamide in 350ml of THF. After addition of the hydride is complete, the reaction is allowed to warm to room temperature and is stirred for 30 minutes. The thickened reaction mixture is cooled to 0° to 5° C. and is then added dropwise over 30 minutes to a solution of 30 grams of p-pivaloylbenzoyl chloride in 50 ml of dry THF. The resulting solution is stirred for 15 minutes at 0° to 5° C. and is then quenched with 150 ml of saturated ammonium chloride solution. The THF phase is decanted off, and the aqueous phase is extracted with ethyl acetate. The ethyl acetate extract is combined with the THF phase, dried with magnesium sulfate, filtered, and then evaporated almost to dryness. The resulting solids are triturated with ether, and the white crystals obtained are filtered, washed with ether and dried to yield the title product (m.p. 137°–138° C.).

When the above process is carried out using in place of the 3-phenylpropionamide, an equivalent amount of:
a) acetamide;
b) octanoylamide; or
c) 3-phenylacrylamide, there is obtained
a) 4-(2,2-dimethyl-1-oxopropyl)-N-acetylbenzamide (m.p. 88°–89° C.);
b) 4-(2,2-dimethyl-1-oxopropyl)-N-octanoylbenzamide (m.p. 87°–89° C.); or
c) 4-(2,2-dimethyl-1-oxopropyl)-N-(3-phenylacrylyl)-benzamide (m.p. 178°–180° C.), respectively.

EXAMPLE 14

4-(2,2-dimethyl-1-oxopropyl)-N-[4-(2,2-dimethyl-1-oxopropyl)-benzoyl]-benzamide

A solution of 12.3 grams (60 mmol) of 4-(2,2-dimethyl-1-oxo-propyl)-benzamide dissolved in 450 ml of THF is chilled to 5° C.; and 20.6 grams of 35% potassium hydride in oil washed twice with hexane is added as a suspension in hexane. The resulting mixture is stirred for hours at 5° C. A solution of 13.8 grams (61.4 mmol) of p-pivaloyl-benzoyl chloride dissolved in 100 ml of THF is added with stirring over a period of 2½ hours at 5° C. Sitrring is continued for an additional hour at this temperature, following which the mixture is stirred into 500 ml of an ice-cold saturated NH4Cl solution. The liquid phases are separated, and the aqueous phase is extracted with t-butyl methyl ether. The combined organic layers are washed with saturated sodium chloride solution, separated, and dried over magnesium sulfate. After filtering off the magnesium sulfate, the filtrate is evaporated to a solid, and the crude product is partially purified by chromatography on silica with CHCl3 eluant. The resulting product is twice crystallized from isopropyl alcohol and then from methylene chloride/t-butyl methyl ether, yielding the title product (mp 132°–134° C.).

Following the above procedure, but using in place of the 4-(2,2-dimethyl-1-oxopropyl)-benzamide an equivalent amount of 4-(2,2-dimethyl-1-oxopropyl)-N-methyl-benzamide, there is obtained 4-(2,2-dimethyl-1-oxopropyl)-N-methyl-N-[4-(2,2-dimethyl-1-oxopropyl)-benzoyl]-benzamide (m.p. 121.5°–122.5° C.).

EXAMPLE 15

4 (2,2-dimethyl-1-oxopropyl)-N,N-bis-[4-(2,2-dimethyl-1-oxopropyl)-benzoyl]-benzamide A solution of 40.0 gram (0.195 mol) of p-pivaloylbenzamide in 1000 ml of anhydrous THF is cooled to 0° C. and added to a hexane slurry containing potassium hydride from 52.2 grams of a 35% suspension in oil washed with hexane. The mixture is stirred for about 2 hours at 0° C. until hydrogen evolution subsides and then is added with stirring at 0° C. to 5° C. to a solution of 97.3 grams (0.433 mol) of p-pivaloylbenzoyl chloride in 400 ml of THF. The reaction mixture is stirred for 3 hours at 0° C., then warmed to room temperature and stirred overnight. The mixture is evaporated to near dryness under reduced pressure, and the residue is partitioned between chloroform and water. The aqueous phase is extracted twice with chloroform, and the organic phases are combined and dried over magnesium sulfate. After filtering off the magnesium sulfate, the filtrate is evaporated under reduced pressure and redissolved in a minimum amount of chloroform. Ether is added to promote crystallization, and after cooling to complete the process, the mixture is filtered. The white crystalline residue obtained is washed with ether to yield the title product (m.p. 185° to 188° C.).

EXAMPLE 16

4-(2,2-dimethyl-1-oxopropyl)-N-methoxy-N-[4-(2,2-dimethyl-1-oxopropyl)-benzoyl]-benzamide To a suspension of 0.64 grams(80 mmol) of lithium hydride in 150 ml of toluene, 9.4 grams (40 mmol) of solid 4- (2,2-dimethyl-1-oxopropyl)-N-methoxybenzamide is added portion-wise at room temperature and stirred for 1 ½ hours. To this suspension, 9.93 grams (44.2 mmol) of 4- (2,2-dimethyl-1-oxopropyl)-benzoyl chloride dissolved in 50 ml of toluene is added at room temperature. The reaction mixture is stirred for 60 hours and then heated at 65°–70° C. for 22 hours. The mixture is poured into 250 ml. of cold pH7 phosphate buffer under nitrogen and the aqueous phase is then separated and extracted twice with t-butyl methyl ether. The organic layers are washed with dilute sodium bicarbonate solution and after drying over magnesium sulfate, the organic phase is evaporated to dryness. The crude product is crystallized from t-butyl methyl ether/heptane and then recrystallized 3 times from toluene/heptane. After each recrystallization, the nugget-like crystals, enriched in the desired product, are physically separated from the powdery crystals to yield the title compound (m.p. 103°–105 ° C. ).

EXAMPLE 17

4-(2,2-dimethyl-1-hydroxypropyl)-N-(3-phenyl-propionyl-benzamide

In a mixture of 600 ml of absolute alcohol and 400 ml of methylene chloride, 21.4 grams (63.5 mmol) of 4-(2,2-dimethyl-1-oxopropyl)-N-(3-phenylpropionyl)-benzamide is dissolved; and while stirring, 2.4 grams (66.5 mmol) of sodium borohydride are added portionwise over a 5 minute period at a temperature between −20° and −30° C. After 10 minutes, an additional 250 milligrams (3.51 mmol) of sodium borohydride is added and stirring is continued for 15 minutes. The reaction mixture is cooled to −40° C. and quenched with 200 ml of 2N hydrochloric acid followed by 200 ml of water. White crystals form and are filtered off, washed with water, and dried to yield the title product. The filtrate is evaporated down to a small volume; and the white crystals which form are again filtered, washed with water, and dried. The products are combined and recrystallized from ethanol/methylene chloride to yield the pure title compound (m.p. 179.5°–180.5° C.).

Preferred groups of compounds of formula (I) are those in which substituents R, A, B, X, Y, $R_2$, $R_3$, and $R_4$ have the following significances:
a) R is $CH_3$-;
b) A and B are each hydrogen;
c) X is >CO;
d) x is

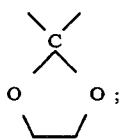

e) X is

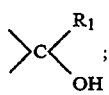

f) X is >CH$_2$;
g) X is —O—;
h) X is >CF$_2$;
i) Y is —OH;
j) Y is —OR$_2$;
k) Y is —NR$_3$R$_4$;
l) R$_2$ is lower alkyl;
m) R$_5$ is hydrogen or lower alkyl;
n) R$_5$ is hydrogen, lower alkyl or phenyl;
o) R$_5$ is hydrogen and R$_6$ is substituted or unsubstitued phenyl and
p) R$_5$ is hydrogen or lower alkyl and R$_6$ is —COR$_{13}$.

What is claimed:
1. A compound of the formula

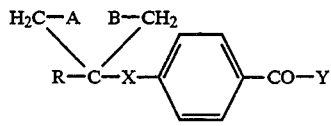

where
R is CH$_3$(CH$_2$)$_m$—,
A and B are each hydrogen or together are a bond or —(CH$_2$)$_n$,
X is

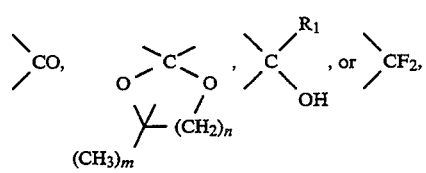

m is 0,1,2 or 3 and n is 1,2 or 3,
R$_1$ is hydrogen or lower alkyl, and
a)
Y is —OH, or —OR$_2$,
where
R$_2$ is lower alkyl, phenyl, phenalkyl of 7 to 9 carbon atoms, —(CH$_2$)$_n$—CONR$_3$R$_4$, —(CH$_2$)$_n$—OCOR$_3$, —(CH$_2$)$_n$—NR$_3$R$_4$ or

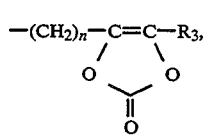

and
R$_3$ and R$_4$ are independently hydrogen or lower alkyl, with the proviso that when X is >CO and A and B are both hydrogen, Y is other than —OH or —OR$_2$, where R$_2$ is lower alkyl; or b)
Y is —NR$_5$R$_6$,
where i) R$_5$ is hydrogen or lower alkyl,
R$_6$ is hydrogen, lower alkyl, —(CH$_2$)$_m$—SH, or —CHR$_7$—COOR$_3$ and
R$_7$ is hydrogen, lower alkyl or

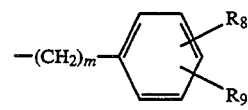

where R$_8$ and R$_9$ are each independently hydrogen, hydroxy, halogen, lower alkyl or lower alkoxy, and m, n, and R$_3$ are as defined above; or
ii) R$_5$ is hydrogen, lower alkyl, —COR$_{10}$ or

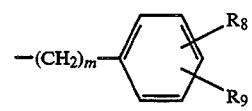

where R$_{10}$ is lower alkyl or —OR$_3$, and m, R$_3$, R$_8$ and R$_9$ are as defined above, and

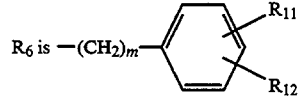

where R$_{11}$ and R$_{12}$ are each independently hydrogen, halogen, lower alkyl, lower alkoxy, —CF$_3$, —(CH$_2$)$_m$COOR$_3$, —CONR$_3$R$_4$, —SO$_3$H or —PO$_3$H$_2$, and m, R$_3$ and R$_4$ are as defined above or
iii) R$_5$ is hydrogen, lower alkyl, —OR$_3$,

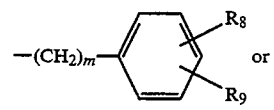

or

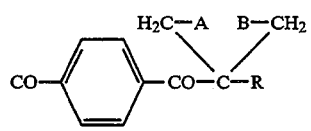

where m, A, B, R, R$_3$, R$_8$ and R$_9$ are as defined above and R$_6$ is —COR$_{13}$,
where R$_{13}$ is alkyl of 1 to 8 carbon atoms, phenalkenyl of 8 to 10 carbon atoms,

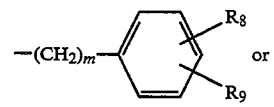

or

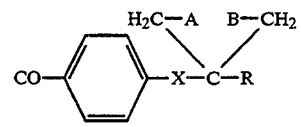

where m, A, B, R, $R_8$ and $R_9$ are as define above, or a pharmaceutically acceptable metal salt or acid addition salt thereof.

2. A compound according to claim 1, in which X is >CO.

3. A compound according to claim 1, in which Y is as defined in group bi.

4. A compound according to claim 1 in which Y is as defined in group bii.

5. A compound according to claim 1 in which Y is as defined in group biii.

6. A compound according to claim 3, in which X is >CO.

7. A compound according to claim 4, in which X is >CO.

8. A compound according to claim 5, in which X is >CO.

9. A compound according to claim 1 of the formula $$\text{H}_2\text{C-A} \quad \text{B-CH}_2$$
$$\text{R-C-CO-} \langle \text{phenyl} \rangle \text{-COOH}$$

where R, A and B and the proviso are as defined in claim 1.

10. A compound according to claim 9 which is 4-(1-methylcyclopropylcarbonyl)-benzoic acid or 4-(2,2-dimethyl-1-oxobutyl)-benzoic acid.

11. A compound according to claim 1 of the formula $$\text{H}_2\text{C-A} \quad \text{B-CH}_2$$
$$\text{R-C-CO-} \langle \text{phenyl} \rangle \text{-COOR}_2$$

where R, A, B, $R_2$ and the proviso are as defined in claim 1.

12. A compound according to claim 11, which is
a) 4-(2,2-dimethyl-1-oxopropyl)-benzoic acid, (2-diethylamino)ethyl ester
b) 4-(2,2-dimethyl-1-oxopropyl)-benzoic acid, (2,2-dimethyl-1-oxopropoxy)methyl ester
c) 4-(2,2-dimethyl-1-oxopropyl)-benzoic acid, (5-methyl-2-oxo-1,3-dioxol-4-yl)methyl ester or
d) 4-(2,2-dimethyl-1-oxoproyl)-benzoic acid, (2-diethylamino-2-oxo)ethyl ester.

13. A compound according to claim 1 of the formula $$\text{H}_2\text{C-A} \quad \text{B-CH}_2$$
$$\text{R-C-CO-} \langle \text{phenyl} \rangle \text{-CON}\langle \begin{array}{c} R_5 \\ R_6 \end{array}$$

where R, A, and B are as defined in claim 1 and $R_5$ and $R_6$ are as defined in group bi.

14. A compound according to claim 13 which is
a) 4-(2,2-dimethyl-1-oxopropyl)-N,N-dimethylbenzamide
b) 4-(2,2-dimethyl-1-oxopropyl)-N-methylbenzamide
c) 4-(2,2-dimethyl-1-oxopropyl)-N-(1,1-dimethylethyl)benzamide
e) 4-(2,2-dimethyl-1-oxopropyl)-N-(2-mercaptoethyl)benzamide
f) 4-(1-methylcyclopropylcarbonyl)benzamide
g) 4-(2,2-dimethyl-1-oxobutyl)benzamide
h) 4-(2,2-dimethyl-1-oxopropyl)benzamide
i) 4-(2,2-dimethyl-1-oxopropyl)benzoyl-(L)phenylalaninamide
j) 4-(2,2-dimethyl-1-oxopropyl)benzoyl-(D)-phenylalaninamide or
k) 4-(2,2-dimethyl-1-oxopropyl)benzoyl-glycinamide.

15. A compound according to claim 1 of the formula $$\text{H}_2\text{C-A} \quad \text{B-CH}_2$$
$$\text{R-C-C-} \langle \text{phenyl} \rangle \text{-COY}$$
$$\text{O} \quad \text{O}$$
$$\diagdown(\text{CH}_2)_n$$
$$(\text{CH}_3)_m$$

where R, A, B, m, n and Y are as defined in claim 1.

16. A compound according to claim 15, which is
a) 2-(4-carboxyphenyl)-2-(1-methylcyclopropyl)-1,3-dioxolane
b) 2-(4-carboxyphenyl)-2-(1,1-dimethylpropyl)-1,3-dioxolane
c) 2-(1,1-dimethylethyl)-2-(4-ethoxycarbonylphenyl)-1,3-dioxolane
d) 2-[[4-[2-(diethlaminocarbonyl)ethoxy]carbonyl]phenyl]-2-(1,1-dimethylethyl)-1,3-dioxolane
e) 2-(1,1-dimethylethyl)-2-[[4-[(2,2-dimethyl-1-oxopropoxy)methoxy]carbonyl]phenyl]-1,3 dioxolane
f) 2-[4-[2-(diethylamino)ethoxy]carbonylphenyl]-2-(1,1-dimethylethyl)-1,3-dioxolane
g) 2-(1,1-dimethylethyl)-2-[4-[(5-methyl-2-oxo-1,3-dioxol-4-yl)methoxycarbonyl]phenyl]-1,3-dioxolane
h) 2-[(4-carbamoyl)phenyl]-2-(1,1-dimethylethyl)-1,3-dioxolane
i) 2-[(4-dimethylaminocarbonyl)phenyl]-2-(1,1-dimethylethyl)-1,3-dioxolane
j) 2-(1,1-dimethylethyl)-2-[(4-phenylaminocarbonyl)phenyl]1,3-dioxolane
k) 2-[(4-carbamoyl)phenyl]-2-(1-methylcyclopropyl)-1,3-dioxolane
l) 2-[(4-carbamoyl)phenyl]-2-(1,1-dimethylpropyl)-1,3-dioxolane
n) 2-(1,1-dimethylethyl)-2-[4-[(2-mercaptoethyl)aminocarbonyl]phenyl)-1,3-dioxolane
o) 2-(1,1-dimethylethyl)-2-(4-carboxyphenyl)-1,3-dioxolane
p) 4-(2-[1,1-dimethylethyl]-1,3-dioxolan-2-yl)benzoyl glycinamide or
q) 4-(2-[1,1-dimethylethyl]-1,3-dioxalan-2-yl)benzoyl glycinamide, methyl ester.

17. A compound according to claim 1 of the formula $$\text{H}_2\text{C-A} \quad \text{B-CH}_2$$
$$\text{R-C-C-} \langle \text{phenyl} \rangle \text{-COY}$$
$$R_1 \quad \text{OH}$$

where R, A, B, $R_1$ and Y are as defined in claim 1.

18. A compound according to claim 17 which is a) 4-carboxy-α-(1,1-dimethylpropyl)-benzenemethanol
b) 4-[(2-diethylamino-2-oxoethoxy)carbonyl]-α-(1,1-dimethylethyl)-benzenemethanol
c) 4-carbamoyl-α-(1,1-dimethylpropyl)-benzenemethanol
d) α-(1,1-dimethylethyl)-4-[(2-mercaptoethyl)aminocarbonyl]-benzenemethanol
e) 4-carboxy-α-(1,1-dimethylethyl)-benzenemethanol
f) 4-carboxy-α-(1,1-dimethylethyl)-α-methyl-benzenemethanol or
g) 4-(2,2-dimethyl-1-hydroxypropyl)-N-(3-phenylpropionyl)-benzamide.

19. A compound according to claim 1 of the formula

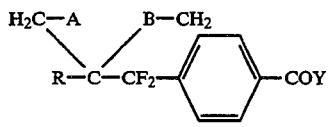

where R, A, B, and Y are as defined in claim 1.

20. A compound according to claim 19, which is
a) 4-(1,1-difluoro-2,2-dimethylpropyl)benzoic acid or
b) 4-(1,1-difluoro-2,2-dimethylpropyl)benzamide.

21. A compound according to claim 1 of the formula

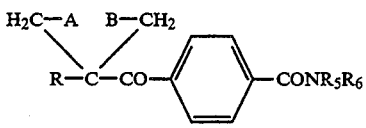

where R, A, and B are as defined in claim 1, and $R_5$ and $R_6$ are as defined in group bii.

22. A compound according to claim 21, which is
a) 4-(2,2-dimethyl-1-oxopropyl)-N-(3-ethoxycarbonylphenyl)-benzamide;
b) 4-(2,2-dimethyl-1-oxopropyl)-N-(2-ethoxycarbonylphenyl)-benzamide;
c) 4-(2,2-dimethyl-1-oxopropyl)-N-(4-tolyl)-benzamide;
d) 4-(2,2-dimethyl-1-oxopropyl)-N-(4-trifluromethylphenyl)-benzamide;
e) 4-(2,2-dimethyl-1-oxopropyl)-N-(4-ethoxycarbonylmethylphenyl)-benzamide;
f) 4-(2,2-dimethyl-1-oxopropyl)-N-(4-sulfophenyl)-benzamide;
g) 4-(2,2-dimethyl-1-oxopropyl)-N-(4-phosphonophenyl)-benzamide;
h) 4-(2,2-dimethyl-1-oxopropyl)-N-(4-carbamoylphenyl)-benzamide;
i) 4-(2,2-dimethyl-1-oxopropyl)-N-(2-methoxy-4-ethoxycarbonylphenyl)-benzamide;
j) 4-(2,2-dimethyl-1-oxopropyl)-N-(2-chloro-4-ethoxycarbonylphenyl)-benzamide;
k) 4-(2,2-dimethyl-1-oxopropyl)-N-(3-bromo-4-ethoxycarbonylphenyl)-benzamide;
l) 4-(2,2-dimethyl-1-oxopropyl)-N-(2-trifluoromethy-4-methoxycarbonylphenyl)-benzamide;
m) 4-(2,2-dimethyl-1-oxopropyl)-N-methyl-N-(4-ethoxycarbonyl-phenyl)-benzamide;
n) 4-(2,2-dimethyl-1-oxopropyl)-N-benzyl-N-(4-ethoxycarbonylphenyl)-benzamide;
o) 4-(2,2-dimethyl-1-oxopropyl)-N-acetyl-N-(4-ethoxycarbonylphenyl)-benzamide;
p) 4-(2,2-dimethyl-1-oxopropyl)-N-ethoxycarbonyl-N-(4-ethoxycarboxylphenyl)-benzamide;
q) 4-(2,2-dimethyl-1-oxopropyl)-N-(4-fluoroplenyl)-benzamide;
r) 4-(2,2-dimethyl-1-oxopropyl)-N-phenylbenzamide;
s) 4-(2,2-dimethyl-1-oxopropyl)-N-(4-carboxyphenyl)-benzamide;
t) 4-(2,2-dimethyl-1-oxopropyl)-N-(4-ethoxycarbonylphenyl)-benzamide;
u) 4-(2,2-dimethyl-1-oxopropyl)-N-benzylbenzamide;
v) 4-(2,2-dimethyl-1-oxopropyl)-N-methyl-N-phenylbenzamide; or
w) 4-(2,2-d imethyl-1-oxopropyl)-N-phenethylbenzamide.

23. A compound according to claim 1 of the formula

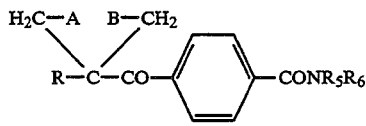

where R, A and B are as defined in claim 1, and $R_5$ and $R_6$ are as defined in group biii.

24. A compound according to claim 23 in which R is methyl and A and B are both hydrogen.

25. The compound according to claim 23 which is 4-(2,2-dimethyl-1-oxopropyl)-N-[4-(2,2-dimethyl-1-oxopropyl)benzoyl]-benzamide.

26. A compound according to claim 23, which is:
a) 4-(2,2-dimethyl-1-oxopropyl)-N-acetylbenzamide;
b) 4-(2,2-dimethyl-1-oxopropyl)-N-octanoylbenzamide;
c) 4-(2,2-dimethyl-1-oxopropyl)-N-(3-phenylacrlyl)-benzamide;
d) 4-(2,2-dimethyl-1-oxopropyl)-N-(3-phenylpropionyl)benzamide;
e) 4-(2,2-dimethyl-1-oxopropyl)-N-methyl-N-[4-(2,2-dimethyl-1-oxopropyl)-benzoyl]-benzamide;
g) 4-(2,2-dimethyl-1-oxopropyl)-N,N-di-[4-(2,2-dimethyl-1-oxopropyl)-benzoyl]-benzamide;
h) 4-(2,2-dimethyl-1-oxopropyl)-N-benzoyl-benzamide; or
i) 4-(2,2-dimethyl-1-oxopropyl)-N-(p-fluorobenzoyl)-benzamide.

27. The compound of claim 17 which is 4-carboxy-α-(1,1-dimethylethyl)-benzenemethanol.

28. A pharmaceutical composition useful in treating diabetes comprising an antidiabetic effective amount of a compound of the formula

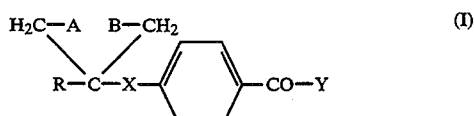

(I)

where R is $CH_3(CH_2)_m$—,
A and B are each hydrogen or together are a bond or —$(CH_2)_n$—, X is 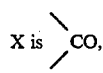

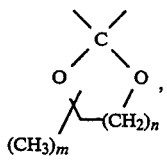

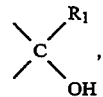

or

m is 0, 1, 2 or 3 and n is 1, 2 or 3,
$R_1$ is hydrogen or lower alkyl, and
a)
Y is —OH or —$OR_2$,
where $R_2$ is lower alkyl, phenyl, phenalkyl of 7 to 9 carbon atoms, —$(CH_2)_n$—$CONR_3R_4$, —$(CH_2)_n$—$OCOR_3$, —$(CH_2)_n$—$NR_3R_4$ or

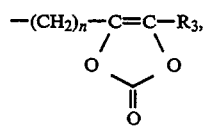

and
$R_3$ and $R_4$ are independently hydrogen or lower alkyl, with the proviso that when X is >CO and A and B are both hydrogen, Y is other than —OH or $OR_2$, where $R_2$ is lower alkyl; or b)
Y is —$NR_5R_6$
where i)
$R_5$ is hydrogen or lower alkyl,
$R_6$ is hydrogen, lower alkyl, —$(CH_2)_mSH$ or —$CH$-$R_7$—$COOR_3$ and
$R_7$ is hydrogen, lower alkyl or

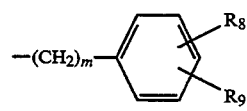

where $R_8$ and $R_9$ are each independently hydrogen, hydroxy, halogen, lower alkyl or lower alkoxy and m, n, and $R_3$ are as defined above; or
ii) $R_5$ is hydrogen, lower alkyl, —$COR_{10}$ or

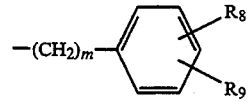

where $R_{10}$ is lower alkyl or $OR_3$ and m, $R_3$, $R_8$ and $R_9$ are as defined above, and

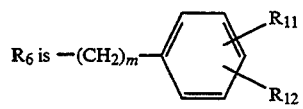

where $R_{11}$ and $R_{12}$ are each independently hydrogen, halogen, lower alkyl, lower alkoxy, —$CF_3$, —$(CH_2)_mCOOR_3$, —$CONR_3R_4$, —$SO_3H$ or —$PO_3H_2$ and m, $R_3$ and $R_4$ are as defined above or
iii) $R_5$ is hydrogen, lower alkyl, —$OR_3$,

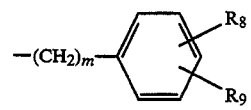

or

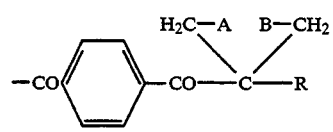

where m, A, B, R, $R_3$, $R_8$ and $R_9$ are as defined above and $R_6$ is —$COR_{13}$,
where $R_{13}$ is alkyl of 1 to 8 carbon atoms, phenalkenyl of 8 to 10 carbon atoms,

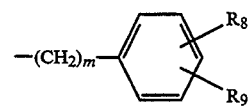

or

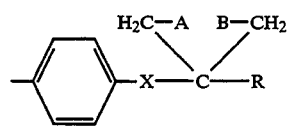

where m, A, B, R, $R_8$ and $R_9$ are as defined above, or a pharmaceutically acceptable metal salt or acid addition salt thereof and a pharmaceutically acceptable carrier therefor.

* * * * *